United States Patent [19]

Inoue

[11] Patent Number: 4,629,645
[45] Date of Patent: Dec. 16, 1986

[54] MOLD INHIBITIVE COATED FILM WITH POWDER COATING MATERIAL USED

[76] Inventor: Tetsuhiko Inoue, 2-37-8, Mukohgaoka, Bunkyo-ku, Tokyo, Japan

[21] Appl. No.: 575,796

[22] Filed: Feb. 1, 1984

[30] Foreign Application Priority Data

Feb. 7, 1983 [JP] Japan ................................ 58-17410

[51] Int. Cl.$^4$ .............................................. B32B 3/00
[52] U.S. Cl. .................... 428/141; 428/143; 428/195; 428/201; 428/202; 428/204; 428/246; 428/251; 428/252; 428/283; 428/284; 428/285; 428/287; 428/343; 428/344; 428/354; 428/355; 428/402; 428/904.4
[58] Field of Search ............... 428/283, 343, 354, 402, 428/904.4, 141, 143, 195, 201, 202, 204, 246, 251, 252, 284, 285, 287, 344, 355

[56] References Cited

U.S. PATENT DOCUMENTS

| | | | |
|---|---|---|---|
| 3,616,146 | 10/1971 | Gabet | 428/904.4 |
| 3,620,366 | 11/1971 | Parkman et al. | 428/904.4 |
| 3,663,269 | 5/1972 | Fischer et al. | 428/904.4 |
| 4,162,237 | 7/1979 | Hauderer | 428/904.4 |
| 4,349,593 | 9/1982 | Blechsten | 428/904.4 |
| 4,361,452 | 11/1982 | Clarke et al. | 428/904.4 |

*Primary Examiner*—James J. Bell
*Attorney, Agent, or Firm*—Stevens, Davis, Miller & Mosher

[57] ABSTRACT

A new mold inhibitive coated film adapted to be adhesively stuck to an object such as wall, ceiling or the like is disclosed. The coated film is constructed in the form of a composite layered structure which essentially comprises a flexible fibrous base material, a layer of adhesive or tackifier coated over the one surface of the base member, a layer of liquid coating material coated over the other surface of the base material and a layer of powder coating material distributed over the coated layer of liquid coating material. Each of adhesive or tackifier, liquid coating material and powder coating material has mold inhibitor included therein. Powder coating material is preferably distributed by natural gravity falling or by electrostatically charging each particle thereof. Alternatively, powder coating material may be distributed directly over the coated layer of adhesive. A separator adapted to be peeled off when it is in use is removably attached to the exposed surface of adhesive. A method of producing a coated film having mold inhibitive or killing powder is also disclosed. Powder coating material is preferably distributed while liquid coating material is kept still in the liquid state and it is integrally stuck to the latter by way of heating, melting and hardening.

15 Claims, 2 Drawing Figures

MOLD INHIBITIVE COATED FILM WITH POWDER COATING MATERIAL USED

BACKGROUND OF THE INVENTION

1. Field of the Invention

The present invention relates to a mold inhibitive coated film adapted to be adhesively stuck onto an object such as wall, ceiling or the like with powder coating material included therein and more particularly to a mold inhibitive coated film fungicide with powder coating material included therein which is easy to be treated or handled in field and has excellent coated film properties in respect of durability, waterproofness and chemical resistibility. Further, the present invention relates also to a method of producing a mold inhibitive coated film of the above-mentioned type. It should be noted that a coated film as referred to in the present invention represents a film constructed of hardened coating material.

2. Description of the Prior Art

As is hitherto known, either water based or solvent based mold inhibitive coating material is prepared by adding mold inhibitive medicine to liquid coating material and mixing them together and it is practically used by coating the mixture over the surface of an object and then causing it to harden. However, the conventional mold inhibitive coating material fungicide has drawbacks that there takes place scattering of liquid coating material during coating operation, it takes a long time until the coated surface is dried and highly trained skill or technique is required for carrying out coating operation due to necessity for handling solvent harmful to the operator or user. When the conventional mold inhibitive fungicide is to be applied to surface area where mold has grown, there is a fear that mold continues to grow until it destroys a layer of mold inhibitive coating material, unless a plurality of preliminary steps of killing the mold, cleaning or bleaching the color of the dead mold and covering the clean surface with a mold inhibitive fungicide are practiced. On the other hand, powder coating material is practically used for highly severe fields of applications where liquid coating material is usable only with much difficulties because it has excellently high coating material properties in respect to durability, waterproofness and chemical resistability, but it is not a coating material which can be easily handled by anybody in field because a specially designed coating apparatus is required and coating operation cannot be performed in field.

SUMMARY OF THE INVENTION

Thus, the present invention has been made with the foregoing drawbacks in mind and its object resides in providing a new mold inhibitive coated from adapted to be adhesively stuck to an object such as wall, ceiling or the like with mold inhibitive fungicide used therefor which can be easily treated or handled in the field without any highly trained skill or technique as required in case of the conventional liquid mold inhibitive fungicide, has no necessity for carrying out preliminary steps of sterilizing, decoloring and bleaching when it is to be applied to surface area on which mold has grown and moreover has excellently high coated film in respect of durability, waterproofness and chemical resistibility.

To accomplish the above object there is proposed according to one aspect of the invention a mold inhibitive coated film adapted to be adhesively stuck onto an object such as wall, ceiling or the like with a mold inhibitive fungicide used therefor which essentially comprises a thin layer of flexible fibrous base material, adhesive or tackifier uniformly coated over the one surface of the fibrous base material and impregnated into the latter, said adhesive having fungicide included therein, liquid coating material uniformly coated over the other surface of the fibrous base material and impregnated into the latter, said liquid coating material being such that it has flexibility after it hardens, and powder coating material uniformly distributed over the coated layer of liquid coating material to be stuck to the latter by way of heating, melting and hardening, said powder coating material being such that it has flexibility after it hardens and having mold fungicide included therein.

Generally, the powder coating material is distributed over the coated layer of liquid coating material while the latter is kept still in the liquid state.

The powder coating material is preferably distributed over the coated layer of liquid coating material with the aid of gravity force of each particle thereof.

The powder coating material may be distributed over the coated layer of liquid coating material while each particle thereof is electrostatically charged.

As required, a separator adapted to be peeled off when the coated film is to be in use removably attached to the exposed surface of adhesive.

Further, to accomplish the above object there is proposed according to other aspect of the invention a mold inhibitive coated sheet adapted to be adhesively stuck to an object such as wall, ceiling or the like with powder coating material used therefor which essentially comprises a thin layer of flexible fibrous base material, adhesive uniformly coated over both the surfaces of the fibrous base material and impregnated into latter, said adhesive or tackifier having mold inhibitive fungicide included therein, and powder coating material uniformly distributed over the one surface of the coated layer of adhesive to be stuck to the latter by way of heating, melting and hardening, said powder coating material being such that it has flexibility after it hardnens and having mold inhibitive fungicide included therein.

As required, a separator is removable attached to the other surface of the coated layer of adhesive.

The powder coating material is distributed over the coating layer of adhesive with the aid of gravity force of each particle thereof or while each particle is electrostatically charged.

Further, to produce a mold inhibitive coated sheet of the first mentioned type there is proposed according to another aspect of the invention a method which essentially comprises the steps of coating adhesive or tackifier over the one surface of a thin flexible fibrous base material and impregnating the former into the latter, said adhesive or tackifier having mold inhibitive fungicide included therein, coating liquid coating material over the other surface of the fibrous base material and impregnating the former into the latter, said liquid coating material being such that it has flexibility after it hardens, and distributing powder coating material over the coated layer of liquid coating material to be stuck to the latter by way of heating, melting and hardening, said powder coating material being such that it has flexibility after it hardens and having mold inhibitive fungicide included therein.

As required, there is provided a step of removably attaching a separator to the exposed surface of adhesive, said separator being peeled off when the coated film is to be in use.

Further, to produce a mold inhibitive coated film of the last mentioned type there is proposed according to another aspect of the invention a method which essentially comprises the steps of coating adhesive over both the surfaces of a thin flexible fibrous base material and impregnating the former into the latter, said adhesive having mold inhibitive fungicide included therein, and distributing powder coating material over one surface of the coated layer of adhesive to be stuck to the latter by way of heating, melting and hardening, said powder coating material being such that it has flexibility after it hardens and having mold inhibitive fungicide included therein.

In case of this type of method a separator is removably attached to the other surface of the coated layer of adhesive as required.

As fibrous base material used for embodying the invention unwoven cloth, woven cloth, composite layered material of unwoven cloth and plastic film and flexible and tough paper are preferably employable. As typical material for unwoven cloth and woven cloth polyester, polyamide, acryl, polyethylene, polypropylene, rayon, glass fiber and metallic fiber of copper or the like metal are preferably employable.

A thickness of fibrous base material is generally determined in the range of 10 to 300 microns. If it is less than 10 micron, it is of insufficient strength. On the other hand, if it is in excess of 300 microns, it results lack of flexibility.

With respect to liquid coating material used for embodying the invention it is necessary that flexibility is maintained after it hardens. Concretely speaking, urethane based liquid coating material, phthalic acid based liquid coating material and rubber based liquid coating material are prefeerably employable. Further, another liquid coating material which becomes soft by adding plasticizer thereto, for instance, polyvinylchloride based coating material is acceptable.

A thickness of coated layer of liquid coating material is generally determined in the range of 30 to 100 microns. A part of liquid coating material is impregnated into flexible fibrous base material which it is filled in the space defined between adjacent fibers.

To cover the surface of fibrous base material with liquid coating material a variety of methods are employable by operating spray gun, roll coater, flow coater, knife coater or the like means.

Incidentally, the reasons why liquid coating material is used for practicing the first mentioned method of the invention will be noted below.

(1) In the method of the invention it is necessary that powder coating material is uniformly distributed over the coated layer of base material. By covering the coated layer of base material with liquid coating material adhesiveness of tackiness of powder coating material can be substantially improved and distribution of the same may be effected in an inexpensive coat by natural gravity falling. In this connection it is preferable that powder coating material with mold inhibitive material included therein is distributed over the coated layer of liquid coating material while the latter is kept still in the unsolidified state. (It should be added that powder coating material can be stuck onto the surface layer of liquid coating material by electrostatically charging each particle powder coating material even after liquid coating material is solidified.)

(2) When the liquid coating material is colored with the same color as that of powder coating material, the results is that a coated film of the invention has increased concealing power.

(3) When liquid coating material is colored with required color and powder coating material is colored with transparent color (natural color), it results that color of liquid coating material has increased durability while keeping fine color tone inherent to the liquid coating material.

It is confirmed that further improvement is assured for a mold inhibitive coated film of the invention by including a mold inhibitor in and well mixed with the liquid coating material.

With respect to the powder coating material to be used for embodying the invention it is necessary that it exhibits flexibility after it is solidified. Typically, ethylene vinyl acetate based powder coating material, polyurethane based powder coating material and polyolefine based powder coating material are preferably employable.

A thickness of layer of powder coating material is generally determined in the range of 30 to 200 microns. After the powder coating material is solidified, it is often found that an interface extending between both the layers of powder coating material and liquid coating material located beneath the former becomes visually unrecognizable. It is preferable from the viewpoint of purport of the invention that mold inhibitive fungicide is well mixed with resin during the step of preparing the powder coating material.

To heat and melt powder coating material conventional drying oven, infrared ray radiation heating apparatus, hot air circulation type drying oven or the like apparatus are preferably employable each of which has been satisfactorily used for drying liquid coating material. Drying apparatuses as mentioned above are operated under the working conditions of temperature in the range of 100° to 200° C. and drying time in the range of 1 to 20 minutes. Incidentally, it is recommendable that prior to heating and melting powder coating material that any extra of powder coating material is removed by air blowing or recovered with the aid of suction. This leads to material saving and beautiful and uniform surface of powder coating material. After powder coating material is heated and molten, it is caused to cool naturally so that a continuously extended smooth surface of solidified powder coating material is formed.

As adhesive or tackifier to be used for embodying the invention acetic acid vinyl based or glue based adhesive or tackifier which becomes activated by wetting it with water or alcohol, heat sensitive type adhesive such as acrylic resin based adnesive or the like and pressure sensitive type adhesive such as acrylic resin based adhesive, rubber based adhesive or the like are preferably employable. The adhesive is required to have flexibility after it is solidified. Otherwise, storage, transportation and field operation are carried out only with inconvenience and difficulty.

Further, by coloring the adhesive with black, grey, dark brown or dark green using carbon black, pigment, die or the like it is possible to completely conceal dirty or unpleasant color on the surface of an object onto which a coated film of the invention is to be adhesively stuck. For instance, in case where dark mold irregularly grows over a white wall (object to be treated) it is possible to completely conceal the irregularly colored surface of the wall with mold grown thereon by adhesively sticking a plurality of coated films of the invention which include adhesive colored with black or dark green. The rate of addition of pigment or die is preferably selected in the range of 3 to 10% by weight. If the rate of addition is less than the above-defined range, there is a lack of concealing power and therefore the objective of addition of pigment or die falls to be accomplished. On the other hand, if it is in excess of the range, the adhesive has reduced adhesive power.

When adhesive is used for the product of the invention, a separator is not often required. On the other hand, when tackifier is used for the same, a separator is required to protect the exposed surface thereof from any damage or injury. A thickness of adhesive is usually determined in the range of 50 to 100 microns. A part of adhesive or tackifier is impregnated into fibrous base material while it penetrates into the interteses between adjacent fibers.

As mold inhibitive medicine to be used for embodying the invention, Nopcocide (commercial name given by Sannopco Inc., U.S.A.) 2-(thidzolyl)-benzimidazole (so-called Thiabendazole, commercial name given by Merck Inc., U.S.A.), Prebentol (commercial name given by Bayer AG, West Germany) and Vinyzene (commercial name given by Ventron Inc., U.S.A.) are particularly employable from the viewpoint of safety, durability (medicinal durability), heat resistance and being efficacious against mold. Although Vinyzene has excellent medicinal effect, addition into the coating material is not permitted in view of safety. However, it has been confirmed that Vinyzene is safely used when it is kneaded with adhesive and therefore it has been put in practical use for a long period of time in the United States. Its fungicidal power is proven by the fact that adhesive with an excessive amount of vinyzene included therein kills mold merely by contact of the latter with the former. In general, so-called mold inhibitive fungicidal is classified into two types, one of them being such that it has only mold inhibitive power and the other one being such that it has both mold inhibitive power and mold killing power. When mold inhibitive fungicide is added into and mixed with adhesive or tackifier, the following considerations should be preferably taken.

(1) Fungicide having only mold inhibitive power (for instance, Nopcocide, Thiabendazole) is added into and mixed with coating material.

(2) Fungicide having both mold inhibitive power and mold killing power (for instance, Prebentol, Vinyzene) is added into and mixed with adhesive.

It should be noted that each of the above-noted mold inhibitive fungicides is prepared in the form of powder.

Rate of addition of mold inhibitive fungicide to liquid coating material and adhesive or tackifier is selected in the range of 0.05 to 10% by weight in the solid state. If the rate of addition is less than the above-defined range, it results that mold inhibitive function fails to work properly, whereas if it in excess of the same, fruitful result cannot be expected. Addition is typically effected by way of the steps of dissolving the mold inhibitive fungicide into a solvent such as toluene, xylene, methyl ethyl ketone or the like and then mixing the latter with another solvent used for liquid coating material and adhesive or tackifier. The rate of addition of mold inhibitive fungicide into the powder coating material is generally determined to be in the range of 0.05 to 10% by weight. Addition of mold inhibitive fungicide is effected by adding mold inhibitive fungicide into the resin during the step of preparing powder coating material. Alternatively, th addition may be effected by mixing together both powder materials of mold inhibitive medicine and resin in a gas circulating tank in accordance with the so-called dry blend method, said gas circulating tank being operated in accordance with the principle of a gas circulating immersion tank.

Any separator is usable for a coated film of the invention as far as it can protect the exposed surface of adhesive from damage or injury. No particular structural limitation is provided for the separator. A thickness of the separator is usually selected to be in the range of 20 to 100 microns. Accordingly, a coated film of the invention will have a thickness in the range of 80 to 400 microns in the finished state when no separator is attached thereto, whereas it have a thickness in the range of 100 to 500 microns in the finished state when a separator is attached thereto.

Other objects, features and advantages of the present invention will become more clearly apparent from reading of the following description which has been prepared in conjunction with the accompanying drawings.

BRIEF DESCRIPTION OF THE DRAWINGS

The accompanying drawings will be briefly described below.

DETAILED DESCRIPTION OF THE EMBODIMENTS

Now, the present invention will be described in a greater detail hereunder with reference to the accompanying drawings which schematically illustrate two preferred embodiments of the invention.

Figure 1:
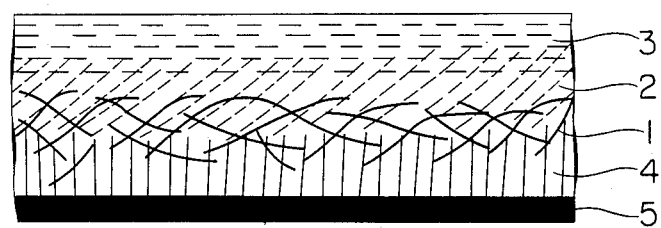
FIG. 1 is a vertical sectional view of a mold inhibitive coated film produced in accordance with the first method of the invention, shown in an enlarged scale.
Figure 2:
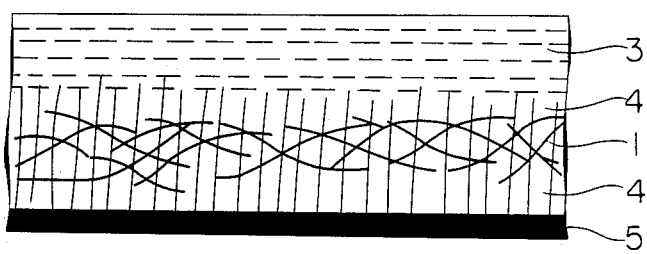
FIG. 2 is a vertical sectional view of a mold inhibitive coated film produced in accordance with the second method of the invention, shown in an enlarged scale.

FIGS. 1 and 2 schematically illustrate by way of a vertical sectional view the layered structure of a mold inhibitive coated film adapted to be used by sticking, wherein the coated film in FIG. 1 is produced in accordance with the first method of the invention using powder coating material and the coated film in FIG. 2 is produced in accordance with the second method of the invention using powder coating material. In the drawings reference numeral 1 designates a thin flexible fibrous base material, reference numeral 2 designates a layer of liquid coating material, reference numeral 3 does a layer of powder coating material with a mold inhibitive fungicide cine included therein, reference numeral 4 does an adhesive with mold inhibitive medicine included therein and reference numeral 5 designates a separator.

First, description will be made below as to the first method of the invention with reference to FIG. 1. The fibrous base material 1 is coated with adhesive 4 over its lower surface so that the latter is impregnated into the former. As required, the lower surface is covered with the separator 5 for the purpose of protecting the coated film. Next, the upper surface of the fibrous base material 1 is coated with liquid coating material 2 so that the latter is impregnated into the former. Further, the coated layer of liquid coating material 2 is added with powder coating material 3 over the whole surface thereof by way of either of two steps, one of them being such that powder coating material with mold inhibitive fungicide included therein is added by uniform distribution under the influence of gravity force of each particle of the powder coating material while the other one being such that each particle of powder coating material is electrostatically charged so as to facilitate uniform sticking to the coated surface of liquid coating material. After completion of the addition of powder coating material 3 over the coated surface of liquid coating material 2 the composite layer of two coating materials 2 and 3 is heated up to an elevated temperature so that powder coating material 3 is molten and thereby both the coating materials 2 and 3 are united to one another. As it is cooled, powder coating material 3 with mold inhibitive fungicide included therein is caused to harden whereby a continuous smooth surface is formed over the composite layer of the two coating materials.

Next, description will be made below as to the second method of the invention with reference to FIG. 2. As will be apparent from the drawing, the fibrous base material 1 is coated with adhesive 4 over both the upper and lower surfaces thereof so that the latter is impregnated into the former. Thereafter, the upper surface of coated adhesive 4 located opposite to the separator 5 is added with powder coating material 3 with mold inhibitive fungicide included therein, wherein addition of powder coating material 3 is carried out by natural gravity falling of each particle thereof. The composite structure comprising fibrous base material 1, adhesive 4, powder coating material 3 and separator 5 is heated so that powder coating material 3 is molten and thereby it is united to adhesive 4. As the composite structure is cooled, powder coating material 3 with mold inhibitive fungicide included therein is caused to harden whereby a continuously extended smooth surface is formed over the composite structure of a coated film.

Cooling may be effected naturally without any aid of cooling means.

After the coated layer of powder coating material is completely solidified, it will be found that a part of mold inhibitive medicine is dispersed within the resin layer constituting the coated film and a part of the same is exposed to the outside on the upper surface of the resin layer but there is no danger that the exposed part of mold inhibitive fungicide becomes disconnected from the coated film.

Next, description will be made below as to how a coated film of the invention is practically put in use.

It has been confirmed that the product of the invention exhibits its advantageous feature especially when it is used at the position where it is impossible to carry out any of conventional powder coating operations. Typical applications are noted as follows:

bath room, dressing room, kitchen, living room oriented to the north or the like in a private house, wall surfaces in a food processing room or factory, storage house, cooking room in an inn or hotel, operation room in a hospital.

Obviously, wall surfaces, ceiling or the like on the aforesaid applications is an area where mold grows easily. When a coated film of the invention with no separator attached thereto is to be used, there is necessity for carrying out preliminary treatment for adhesive on the coated film so as to cause it to be activated. In practice activation is effected by wetting the surface of the adhesive with water or alcohol or heating the same by means of an iron, drier or the like device. When a coated film of the invention with a separator attached thereto is to be used, the latter is peeled off therefrom so that the surface of adhesive becomes exposed to the outside so as to allow it to be stuck to an object such as a wall, ceiling or the like.

Next, description will be made as to characterizing features of a coated film of the invention.

As will be readily understood from the above description, the product of the invention is very easy to be used or treated in field. Namely, field operation is performed without any occurrence of spattering of coating material while no drying time is required. Further, there is no necessity for using solvent harmful to operator or user. In addition to this there is no necessity for arranging a specially designed apparatus as is the case with the conventional powder coating operation. Since the coated film of the invention includes powder coating material of which the continuously extended smooth surface layer has excellent coated film properties in respect of durability, waterproofness and chemical resisting capability are assured and moreover since mold a inhibitive fungicide is included in the coated film, it is possible to prevent any mold from newly growing. When mold inhibitive fungicide having highly effective mold killing power is employed for the adhesive, it results that mold which has grown on an object can be killed by covering the latter with the product of the invention. It should be noted that this sort of operation cannot be performed with any conventional mold inhibitive coating material. Further, it is possible to completely conceal the unpleasant color of mold by using adhesive colored with black, grey, dark green or like color.

Further, owing to the characterizing features of the product of the invention that it is very flexible and has high tensile strength attributable to the existence of fibrous base material it is assured that a coated film is readily deformed in conformance with any type of rugged surface configuration of an object and therefore it can exactly reproduce the original configuration of the latter. As a result, beautiful surface finishing very similar to that of conventional coating operation conducted with liquid coating material can be obtained.

EXAMPLE 1

(1) fibrous base material used—Unicel (commercial name given by Teijin Ltd. which is a producer thereof.
 commercial goods NO.: BT0403W
 material: polyester fiber 70%+polyethylene fiber 30%
 type of product: unwoven cloth
 thickness: approximately 50 microns (2) liquid coating material used—New bodeluch (commercial name given by Nippon Paint Co., Ltd. which is a producer thereof)
 material: phthalic acid based coating material for industrial use
 color: white
 solvent used for coating material: toluene, xylene (3) powder coating material used—Levasint (commercial name given by Bayer AG, West Germany which is a producer thereof)
 material: ethylene vinyl acetate
 grain size: 100 microns in average
 color: white (4) adhesive used—Stract bond SBX-5007 (commercial name given by Mitsui Toatsu Chemicals, Inc. which is a producer thereof)
  material: acrylic acid ester
  color: black colored with carbon black
  solvent used therefor: acetic acid, toluene, IPA (5) fungicide included in powder coating material (in the dry blended state)—TBZ 100 (commercial name given by Merck Inc., U.S.A. which is a producer thereof)
  material: 2-(4-thiazolyl)-benzimidazole amount of material used: 1% (by weight percentage)

(6) mold inhibitive medicine included in adhesive—Vinyzene (commercial name given by Ventrone Inc., U.S.A. which is a producer thereof)
  material: 10-10'-oxybisphenoxyarsine
  solvent used for mold inhibitive medicine: methyl ethyl ketone
  amount of solvent used: 10% (by weight percentage)

(7) amount of adhesive to be coated on and impregnated into unwoven cloth—approximately 1000 microns in thickness.

It should be noted that the first method of the invention is such that no adhesive exudes to the opposite side of the unwoven cloth while the second method of the same is such that it does.

(8) amount of liquid coating material to be coated on and impregnated into unwoven cloth—approximately 50 micron in thickness.

It should be noted that a thickness of coating and impregnation of liquid coating material is determined so as to assure that fibers in the unwoven cloth are recognized visually.

(9) method for distributing powder coating material over the coated layer of liquid coating material to stick the former to the latter—The method is embodied by spraying liquid coating material through a nozzle in the atomized state while it is not still hardened (so-called natural gravity falling method).

An extra amount of powder coating material is removed by air blowing.

(10) condition and method for heating and melting powder coating material—condition: 155° C. and 2 minutes.
  method: hot air circulating type constant temperature oven.

By using the aforesaid materials under the aforesaid conditions coated films were produced in accordance with the first and second methods as described above and they were then tested in the following manner.

Details of tests carried out (1) tensile strength—Tensile tests were conducted in accordance with JIS K 7113 under the operating conditions of 23±2° C. and 100±10 mm/min.

(2) wear proofness—Wear proofness tests were conducted in accordance with Taber's wearing test method.

(3) chemical resistibility—Chemical resistibility of coated films of the invention was tested by immersing them in the following chemicals for a period of 15 days and an amount of erosion was measured with respect to each of the chemicals.

$H_2SO_4$ 10% aqueous solution, $HNO_3$ 10% aqueous solution, HCl 10% aqueous solution, $N_aOH$ 10% aqueous solution, $NH_4OH$ conc., $H_2O_2$ 30% aqueous solution, $CH_3COOH$ 20% aqueous solution, kerosine, table salt 5% aqueous solution, neutral detergent 10% aqueous solution, petroleum and mineral oil (4) Weather proofness—Coated films were subjected to long time tests for a period of 2000 hours using a sunshine weather-O-meter.

(5) heat cycle tests—The tests were conducted under the following conditions.

| temperature | 85° C. | room temp. | −20° C. |
|---|---|---|---|
| time | 15 min | 1 min | 15 min |
| number of cycles | | 20 cycles | |

(6) boiling water test—Coated films were immersed in boiling water for a period of 2 hours.

(7) adhesive sticking power test—This adhesive sticking power test was conducted by way of the steps of cutting test pieces having a width of 20 mm and a length of 100 mm from a coated film of the invention, adhesively sticking one of them onto a plate made of stainless steel with the aid of a rubber roller having a weight of 3 Kg which was caused to move forward and backward by a single cycle and then peeling it off the plate by an angular distance of 180 degrees under the operating conditions of temperature of 20±2° C. and room humidity of 65±15%.

(8) tacky sticking power test—This tacky sticking power test was conducted in accordance with J. Dow's testing method under the operating conditions of angular peeling distance of 30 degrees and temperature of 20° C.

With respect to the testing items (1) to (6) as described above it was confirmed that the products of the invention have coated film properties substantially the same or higher than those of powder coating obtained in accordance with any of conventional methods. Further, with respect to the testing items (7) and (8) a number of tests are being conducted for bath rooms in private houses as well as bath rooms in business buildings (inn, hotel or the like) but it has been observed that no peeling takes place after one year and therefore they have sufficiently excellent properties.

Further, mold inhibition tests were conducted for the products of the invention in the following manner.

(9) bacillus of mold used for the tests (in accordance with MIL E 5272C)
  *Aspergillus niger*
  *Aspergillus flavus*
  *Chaetomium globosum*
  *Penicillium citrinum*
  *Fusarium moniliforme*

(10) method of testing—Liquid with sporule of one of the above-mentioned five kinds of test bacilluses dispersed therein was filled in a sprayer and it was then sprayed over the whole surface area of a test piece by operating the sprayer to such an extent that the surface was appreciably wetted with liquid so that sporule was planted thereon.

(11) test conditions—Mold inhibition tests were conducted under the conditions of temperature of 30±2° C., room humidity of 95±5% and holding time of 28 days. On the 29th day counted from start of testing test pieces were taken out of the testing chamber and it was observed that no mold grew on their surface.

Furthermore, mold killing tests were conducted for the products of the invention in the following manner.

(12) bacillus of mold used for the tests—same to those in the above item (9)

(13) object on which mold was planted—gypsum board

(14) method for planting mold on gypsum board—same as that in the above items (10) and (11). On the 29th day counted from start of testing it was visually observed that mold grew over the whole surface of the gypsum board. The product of the invention was adhesively stuck to the surface under the influence of high compressing force and after one year it was peeled off therefrom. As a result of careful observation it was found that mold was completely dead. The product of the invention had for a while a colored surface and therefore it lacked concealing power for inhibiting an object located beneath the product from being visually recognized. In spite of less concealing power of the product as mentioned above the color of the dead mold on the surface of the gypsum board failed to be observed through the product. This was attributable to the fact that tackifier employed for the product was colored with black.

It has been confirmed from the results of various tests conducted in the above-mentioned manner that in addition to excellent coated film properties inherent to powder coating material the products of the invention have another advantageous features of (1) mold inhibitive power against mold which may or will grow if they are absent, (2) mold killing power against mold which has grown and (3) concealing power for preventing any color of dead mold or other foreign material from being recognized visually. In other words it becomes possible to replace at least three steps of any of conventional mold inhibition operations comprising sterilizing, bleaching and mold inhibiting with a single step of adhesively sticking with the aid of compressing force by an operator.

While the present invention has been described above with respect to preferred embodiments and examples, it should of cource be understood that the present invention should be not limited only to them but various changes or modifications may be made in a suitable manner without any departure from the spirit and scope of the invention.

What is claimed is:

1. An adhesive sheet material to control mold fungi for application to a surface of a wall, floor, ceiling and the like, comprising:
   a flexible fibrous support having thickness of from $10\mu$ to $300\mu$;
   an adhesive layer containing a mold fungicide, on one side of said support;
   a layer of a liquid paint containing a mold fungicide, on the other side of said support; and
   a layer of a powder coating containing a mold fungicide, formed over said layer of the liquid paint.

2. A mold inhibitive coated sheet as defined in claim 1, wherein the powder coating material is distributed over the coated layer of liquid coating material while the latter is kept still in the liquid state.

3. A mold inhibitive coated shut as defined in claim 1, wherein the powder coating material is distributed over the said layer of paint with the aid of of gravity force of each particle thereof.

4. A mold inhibitive coated sheet film as defined in claim 1, wherein the powder coating material is distributed over said layer of paint while each particle thereof is electrostaically charged.

5. A mold inhibitive coated sheet as defined in claim 1, wherein a separator is removably attached to the exposed surface of the adhesive layer so that it may be peeled off when it is to be used.

6. An adhesive sheet material as claimed in claim 1, wherein a separatable protecting film is covered over the surface of the adhesive layer.

7. An adhesive sheet material as claimed in claim 1, wherein said flexible support is selected from the group consisting of unwoven cloth, woven cloth, multi-layered sheet of unwoven cloth and plastic film, and flexible and tough paper.

8. An adhesive sheet material as claimed in claim 1, wherein said adhesive layer comprising adhesive material which is selected from the group consisting of permanently tacky adhesives, solvent releasing adhesives, pressure sensitive adhesives, heat sensitive adhesives and thermosetting adhesives.

9. An adhesive sheet material as claimed in claim 1, wherein said layer of liquid paint contains a coloring material selected from the group of the inorganic pigments, organic pigments and dyes, preferably having deep color, such as black, dark brown, dark green and the like.

10. An adhesive sheet material as claimed in claim 1, wherein the layer of powder coatings containing a coloring material selected from the group of the inorganic pigments, organic pigments and dyes, having preferably deep color, such as black, dark brown, dark green and the like.

11. An adhesive sheet material as claimed in claim 1, wherein said mold fungicide is selected from the group of an organic fungicide and inorganic fungicide, such as derivatives of benzimidazol and derivatives of phenolarsine and the like.

12. An adhesive sheet material to control mold fungi for application to a surface of wall, floor, ceiling and the like, comprising:
    a flexible fibrous support having thickness of from $10\mu$ to $300\mu$;
    an adhesive layer containing a mold fungicide, on both sides of said support;
    a layer of a powder coating containing a mold fungicide, formed over the exposed surface of said adhesive layers.

13. A mold inhibitive coated sheet as defined in claim 12, wherein the powder coating material is distributed over the coated layer of adhesive with the aid of the gravity force of each particle thereof.

14. A mold inhibitive coated sheet as defined in claim 12, wherein the powder coating material is distributed over the coated layer of adhesive while each particle thereof is electrostatically charged.

15. A mold inhibitive coated film as defined in claim 12, wherein a separator is removably attached to the other surface of the coated layer of adhesive so that it may be peeled off when it is to be used.

* * * * *